(12) United States Patent
Ananthan et al.

(10) Patent No.: US 10,675,071 B2
(45) Date of Patent: Jun. 9, 2020

(54) SYSTEM AND METHOD FOR BONE FIXATION USING A PLATE STRADDLED BY A RETAINER

(71) Applicant: Acumed LLC, Hillsboro, OR (US)

(72) Inventors: Bharadwaj Ananthan, Portland, OR (US); Matthew Peter Gephart, Marquette, MI (US); Thomas R. Lyon, Brooklyn, NY (US); Amir Meir Matityahu, Los Altos, CA (US); Andrew Howard Schmidt, Orono, MN (US)

(73) Assignee: Acumed LLC, Hillsboro, OR (US)

( * ) Notice: Subject to any disclaimer, the term of this patent is extended or adjusted under 35 U.S.C. 154(b) by 300 days.

(21) Appl. No.: 15/726,312

(22) Filed: Oct. 5, 2017

(65) Prior Publication Data
US 2018/0098802 A1    Apr. 12, 2018

Related U.S. Application Data

(60) Provisional application No. 62/405,646, filed on Oct. 7, 2016.

(51) Int. Cl.
*A61B 17/80*    (2006.01)
*A61B 17/82*    (2006.01)
(Continued)

(52) U.S. Cl.
CPC ...... *A61B 17/8057* (2013.01); *A61B 17/8033* (2013.01); *A61B 17/842* (2013.01);
(Continued)

(58) Field of Classification Search
CPC .............................. A61B 17/80; A61B 17/82
See application file for complete search history.

(56) References Cited

U.S. PATENT DOCUMENTS 3,842,825 A    10/1974    Wagner
4,973,332 A    11/1990    Kummer
(Continued)

FOREIGN PATENT DOCUMENTS

CN    2169386 Y    6/1994
DE    8628766 U1    12/1986
(Continued)

OTHER PUBLICATIONS

Copenheaver, Blaine R., Authorized Officer, International Searching Authority / US, Commissioner for Patents, "International Search Report" in connection with related International Application No. PCT/US2017/055434, dated Dec. 1, 2017, 2 pgs.
(Continued)

*Primary Examiner* — David W Bates
(74) *Attorney, Agent, or Firm* — K&L Gates LLP

(57) ABSTRACT

Systems and methods for bone fixation using a plate straddled by a retainer. In an exemplary system, the plate may be an elongated plate configured to be disposed longitudinally on a bone. The retainer may have a body interconnecting a pair of mounting regions. The body may define a recess, and each mounting region may define a first aperture and a second aperture. The retainer may be configured to be mated with the plate to position a section of the plate in the recess such that the retainer straddles the plate. The first apertures may be configured to define through-axes that are tangential to the bone, to enable use with a line including wire and/or cable, and each second aperture may be configured to define a through-axis that extends through opposite sides of the bone while avoiding a medullary canal thereof, to enable use with a threaded fastener.

10 Claims, 7 Drawing Sheets

(51) Int. Cl.
*A61B 17/84* (2006.01)
*A61B 17/00* (2006.01)
*A61B 17/56* (2006.01)

(52) U.S. Cl.
CPC ..... *A61B 17/82* (2013.01); *A61B 2017/00004* (2013.01); *A61B 2017/564* (2013.01)

(56) References Cited

U.S. PATENT DOCUMENTS

| | | | |
|---|---|---|---|
| 5,116,335 A | 5/1992 | Hannon et al. | |
| 5,151,103 A | 9/1992 | Tepic et al. | |
| 5,190,545 A * | 3/1993 | Corsi | A61B 17/82 606/309 |
| 5,665,089 A * | 9/1997 | Dall | A61B 17/80 606/309 |
| 6,001,099 A | 12/1999 | Huebner | |
| 6,224,602 B1 | 5/2001 | Hayes | |
| 6,395,030 B1 | 5/2002 | Songer et al. | |
| 6,520,965 B2 * | 2/2003 | Chervitz | A61B 17/842 606/103 |
| 6,755,831 B2 | 6/2004 | Putnam et al. | |
| 7,041,105 B2 | 5/2006 | Michelson | |
| 7,090,676 B2 | 8/2006 | Huebner et al. | |
| 7,255,701 B2 * | 8/2007 | Allen | A61B 17/82 606/74 |
| 7,547,305 B2 | 6/2009 | Rapp | |
| 8,177,819 B2 | 5/2012 | Huebner et al. | |
| 8,226,693 B2 | 7/2012 | Reimels et al. | |
| 8,231,662 B2 | 7/2012 | Huebner | |
| 8,298,271 B2 | 10/2012 | Jacene et al. | |
| 8,337,534 B2 | 12/2012 | Celli et al. | |
| 8,486,114 B2 | 7/2013 | Gillard et al. | |
| 8,632,573 B2 | 1/2014 | Ellis et al. | |
| 8,728,082 B2 * | 5/2014 | Fritzinger | A61B 17/80 606/286 |
| 8,764,809 B2 | 7/2014 | Lorenz et al. | |
| 8,876,824 B2 | 11/2014 | Hearn | |
| 9,131,968 B2 | 9/2015 | Cavallazzi et al. | |
| 9,138,244 B2 | 9/2015 | Mebarak et al. | |
| 9,138,245 B2 | 9/2015 | Mebarak | |
| 9,138,267 B2 | 9/2015 | Cavallazzi | |
| 9,622,799 B2 * | 4/2017 | Orbay | A61B 17/80 |
| 9,999,456 B2 * | 6/2018 | Powell | A61B 17/84 |
| 2004/0225291 A1 * | 11/2004 | Schwammberger | A61B 17/80 606/71 |
| 2005/0049595 A1 | 3/2005 | Suh et al. | |
| 2005/0240187 A1 | 10/2005 | Huebner et al. | |
| 2006/0276896 A1 * | 12/2006 | Fallin | A61B 17/80 623/16.11 |
| 2008/0103501 A1 | 5/2008 | Ralph et al. | |
| 2010/0262194 A1 * | 10/2010 | Wagner | A61B 17/80 606/286 |
| 2011/0118784 A1 | 5/2011 | Baynham et al. | |
| 2013/0090695 A1 * | 4/2013 | Bernstein | A61B 17/808 606/281 |
| 2013/0261674 A1 * | 10/2013 | Fritzinger | A61B 17/808 606/286 |
| 2014/0243841 A1 | 8/2014 | Cavallazzi | |
| 2014/0243907 A1 * | 8/2014 | Cavallazzi | A61B 17/74 606/286 |
| 2016/0066969 A1 * | 3/2016 | Reuter | A61B 17/1728 606/71 |
| 2016/0143663 A1 * | 5/2016 | Schemitsch | A61B 17/683 606/71 |
| 2017/0196607 A1 * | 7/2017 | Shin | A61B 17/80 |

FOREIGN PATENT DOCUMENTS

| | | |
|---|---|---|
| EP | 0934731 A1 | 11/1999 |
| EP | 0934731 B1 | 11/1999 |
| FR | 2704420 A1 | 11/1994 |
| GB | 1517161 A | 7/1978 |
| SU | 1634260 A1 | 3/1991 |
| WO | 2007037774 A1 | 4/2007 |

OTHER PUBLICATIONS

Copenheaver, Blaine R., Authorized Officer, International Searching Authority / US, Commissioner for Patents, "Written Opinion of the International Searching Authorityt" in connection with related International Application No. PCT/US2017/055434, dated Dec. 1, 2017, 11 pgs.

* cited by examiner

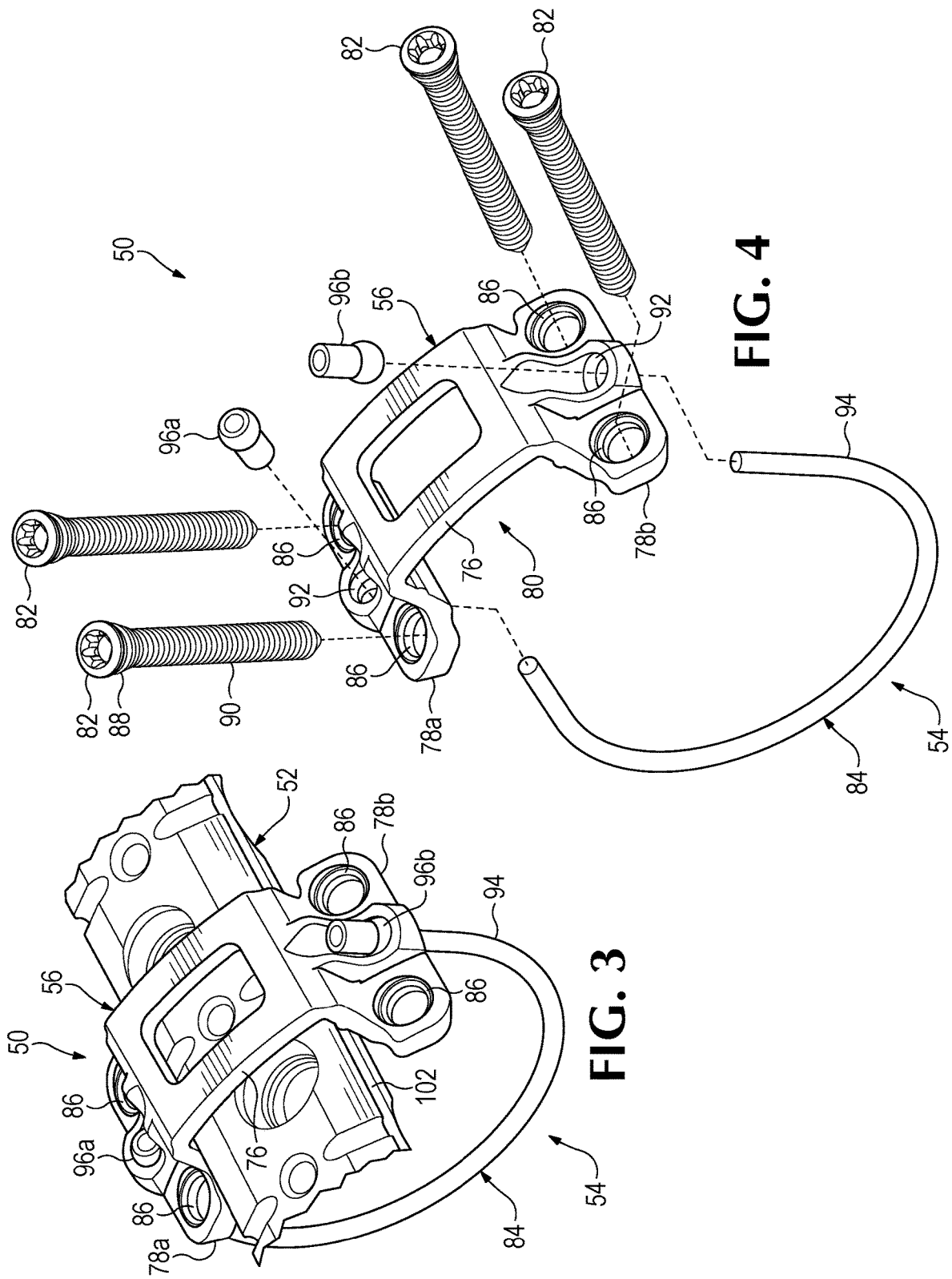

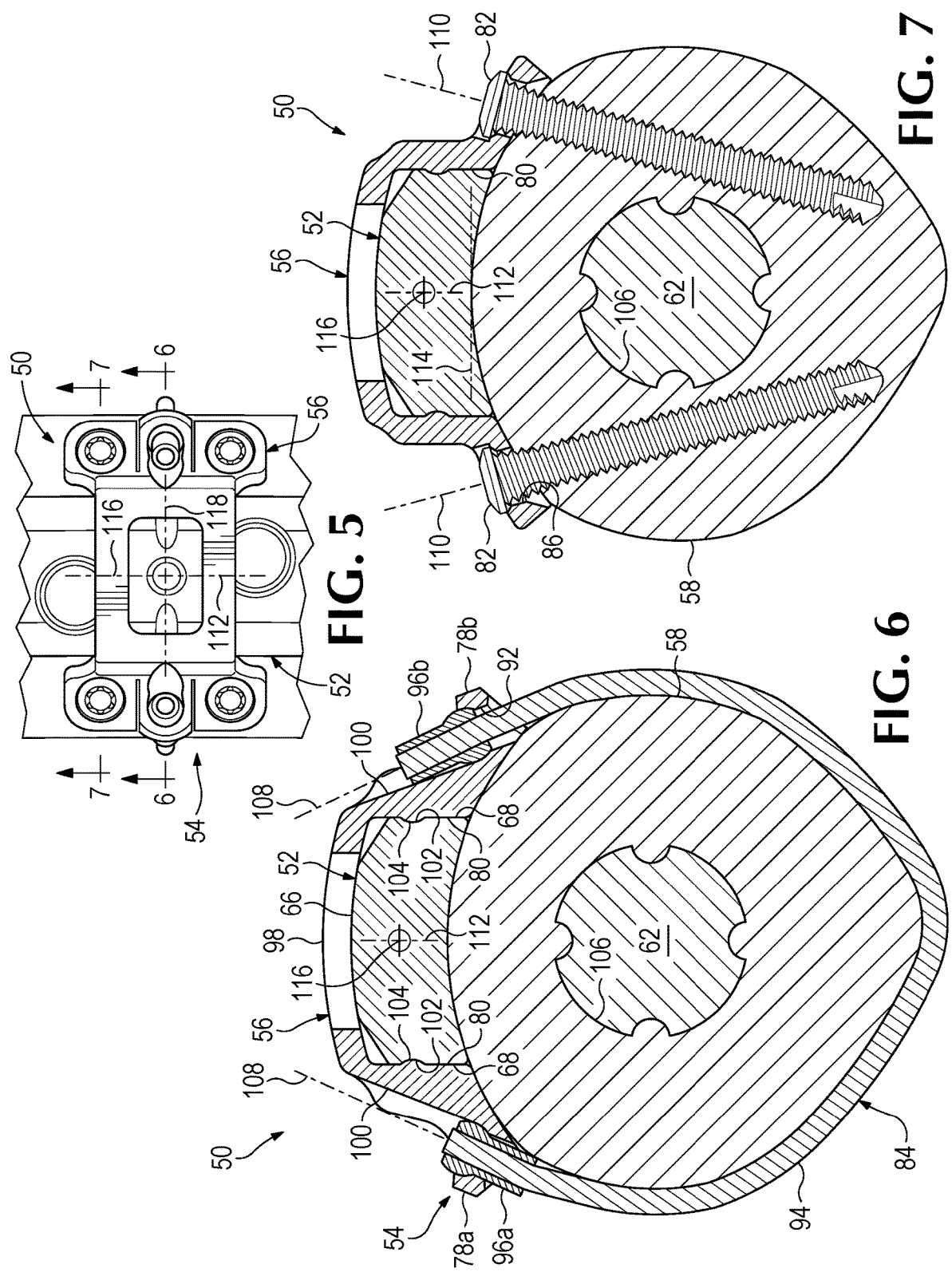

_US 10,675,071 B2_

SYSTEM AND METHOD FOR BONE FIXATION USING A PLATE STRADDLED BY A RETAINER

CROSS-REFERENCE TO PRIORITY APPLICATION

This application is based upon and claims the benefit under 35 U.S.C. § 119(e) of U.S. Provisional Patent Application Ser. No. 62/405,646, filed Oct. 7, 2016, which is incorporated herein by reference in its entirety for all purposes.

INTRODUCTION

A fractured long bone can be fixed with an elongated bone plate secured to the bone with fasteners, such as bone screws, while the bone plate spans one or more fractures. The bone screws may be placed into the bone from a series of apertures arranged along the bone plate. For the best purchase, the screws typically are long enough to extend across the bone's medullary canal, for bicortical engagement with bone.

Achieving bicortical engagement of screws can be problematic when fixing a bone having a peri-prosthetic fracture. In this type of fracture, the fracture line overlaps a previously-installed, underlying prosthesis. Typically, the prosthesis has an intramedullary stem for anchorage, and a head to replace an articulating end of the bone. The stem occupies a section of the medullary canal, thus obstructing a standard bicortical trajectory of bone screws.

Screw trajectories can be moved outside of the bone's medullary canal through the use of an attachment plate mounted over a fixation plate, as disclosed in U.S. Patent Application Publication No. 2010/0262194 A1. The attachment plate is secured separately to the fixation plate and bone, which limits the number of positions at which the attachment plate can be installed. Variations in bone size and geometry can make securing the attachment plate to bone unreliable, thereby reducing the number of positions even further.

SUMMARY

The present disclosure provides systems and methods for bone fixation using a plate straddled by a retainer. In an exemplary system, the plate may be an elongated plate configured to be disposed longitudinally on a bone. The retainer may have a body interconnecting a pair of mounting regions. The body may define a recess, and each mounting region may define a first aperture and a second aperture. The retainer may be configured to be mated with the plate to position a section of the plate in the recess such that the retainer straddles the plate. The first apertures may be configured to define through-axes that are tangential to the bone, to enable use with a line including wire and/or cable, and each second aperture may be configured to define a through-axis that extends through opposite sides of the bone while avoiding a medullary canal thereof, to enable use with a threaded fastener.

BRIEF DESCRIPTION OF THE DRAWINGS

FIG. 3 is a magnified, fragmentary view of the plate and encircling assembly of FIG. 1, taken in the absence of the femur and the threaded fasteners.

FIG. 4 is an exploded view of the encircling assembly and the threaded fasteners of FIG. 1.

FIG. 5 is a magnified, fragmentary top view of the fixation system and femur of FIG. 1, taken around the encircling assembly.

FIG. 6 is a sectional view of the fixation system and femur of FIG. 1, taken generally along line 6-6 of FIG. 5 through the encircling assembly.

FIG. 7 is a sectional view of the fixation system and femur of FIG. 1, taken generally along line 7-7 of FIG. 5 through the retainer at the position of a pair of the threaded fasteners.

DETAILED DESCRIPTION

Figure 1:
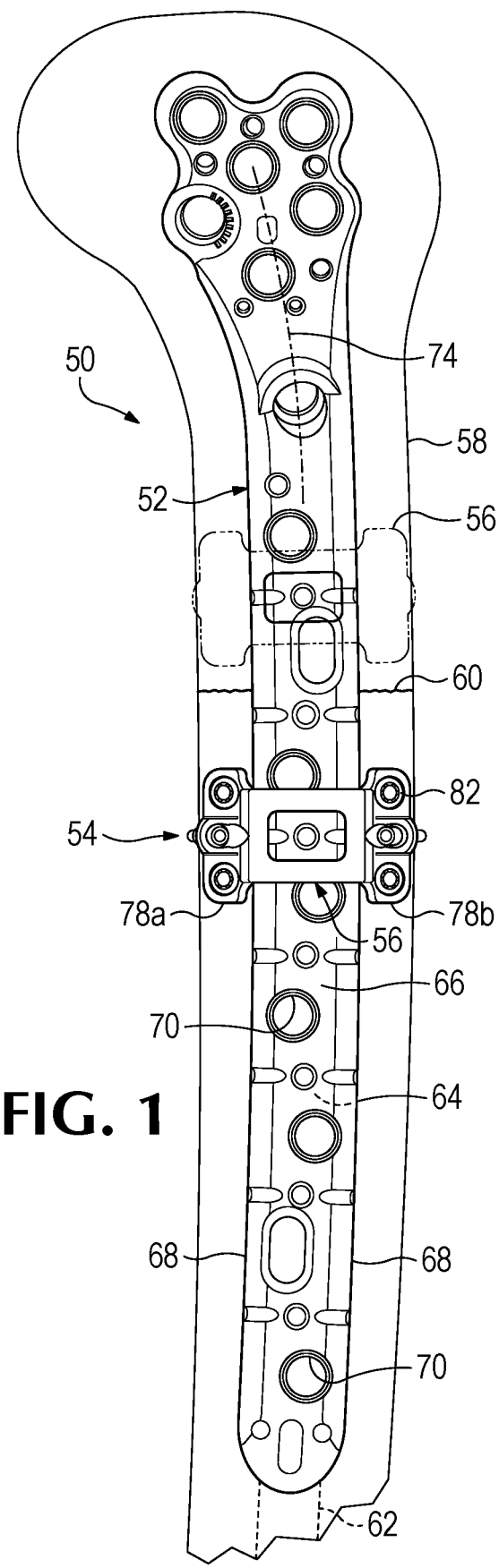
FIG. 1 is a plan view of selected aspects of an exemplary fixation system attached to and stabilizing a fractured left femur that contains an intramedullary implant, where the fixation system includes an elongated fixation plate connected to bone with an encircling assembly, where the encircling assembly includes a retainer and a line (e.g., a cable), and where the retainer straddles the plate and is coupled to the femur using the line and threaded fasteners, in accordance with aspects of the present disclosure.

The present disclosure provides systems and methods for bone fixation using a plate straddled by a retainer. In an exemplary system, the plate may be an elongated plate configured to be disposed longitudinally on a bone. The retainer may have a body interconnecting a pair of mounting regions. The body may define a recess, and each mounting region may define a first aperture and a second aperture. The retainer may be configured to be mated with the plate to position a section of the plate in the recess such that the retainer straddles the plate. The first apertures may be configured to define through-axes that are tangential to the bone, to enable use with a line including wire and/or cable, and each second aperture may be configured to define a through-axis that extends through opposite sides of the bone while avoiding a medullary canal thereof, to enable use with a threaded fastener.

An exemplary system for plate attachment to bone is provided. The system may comprise a plate configured to be disposed on a bone, and a retainer. The retainer may have a first mounting region opposite a second mounting region. The retainer may be configured to straddle the plate such that the first mounting region and the second mounting region project away from opposite lateral edges of the plate. Each of the first mounting region and the second mounting region may define an aperture. The system also may comprise a line and a sleeve. In exemplary embodiments, the line is a cable or wire. The line may be configured to extend from the aperture of the first mounting region to the aperture of the second mounting region, such that the retainer and the line collectively encircle a bone. The sleeve may be configured to be received on the line and crimped to lock the sleeve to the line.

Fixation of a bone having a peri-implant fracture (e.g., a peri-prosthetic fracture) can be challenging. The bone can be stabilized with a wider bone plate designed specifically for peri-prosthetic fractures. However, this bone plate cannot be customized readily for the needs of a given patient having a particular bone size and shape, fracture pattern, and implant. The bone alternatively can be fixed with a fixation plate and an attachment plate. The attachment plate fits over the fixation plate and is configured to be attached to bone with bone screws. However, due to variations in bone geometry, the bone screws often do not provide sufficient anchorage or miss the bone completely.

The systems and methods disclosed herein offer various advantages. For example, the surgeon has more options for attaching a bone plate to bone. Accordingly, the bone plate can be installed more efficiently and securely. Also or alternatively, the bone plate when attached to bone can have the stability of a wider plate but the footprint of a narrower plate.

Further aspects of the present disclosure are described in the following sections: (I) fixation system with plate and retainer, (II) methods of bone fixation and plate attachment, (III) composition of system components, and (IV) selected embodiments.

I. Fixation System with Plate and Retainer

This section describes an exemplary bone fixation system 50 including a plate 52 and an encircling assembly 54 incorporating a plate-straddling retainer 56; see FIGS. 1-16.

Figure 2:
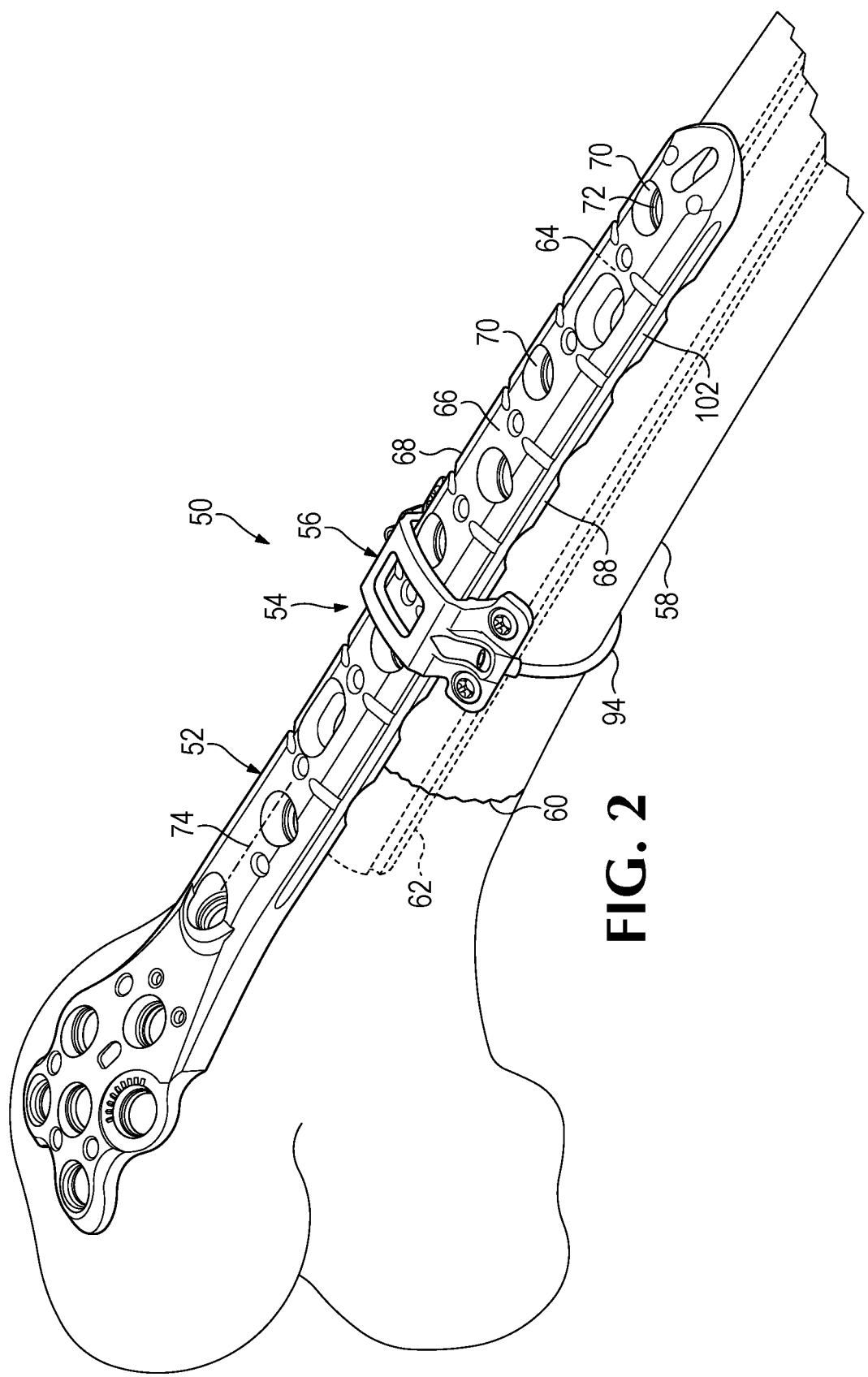
FIG. 2 is another view of the fixation system and femur of FIG. 1, showing the plate and the encircling assembly.
Figure 8:
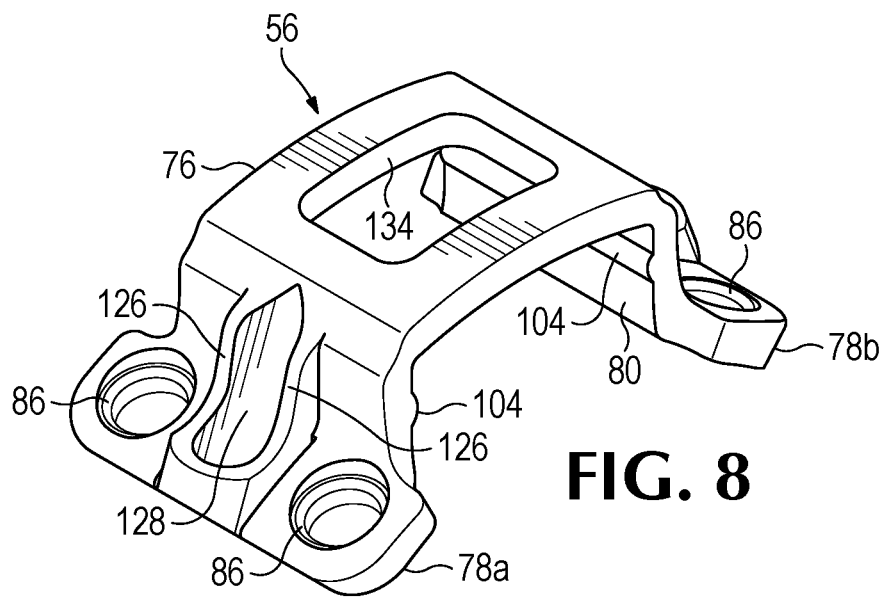
FIG. 8 is an isometric view of the retainer of FIG. 1 taken in isolation.
Figure 9:
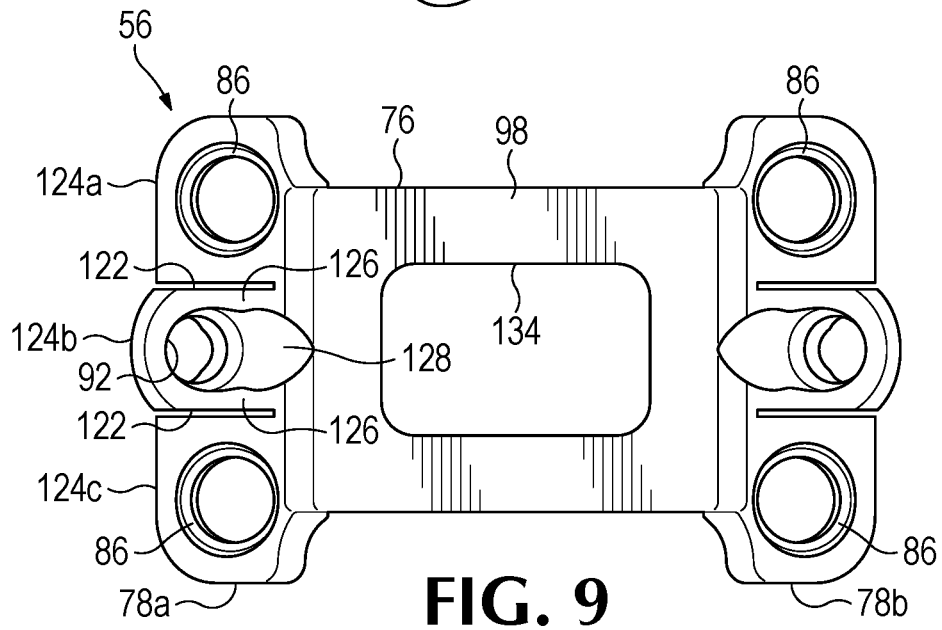
FIG. 9 is a top view of the retainer of FIG. 1.
Figure 10:
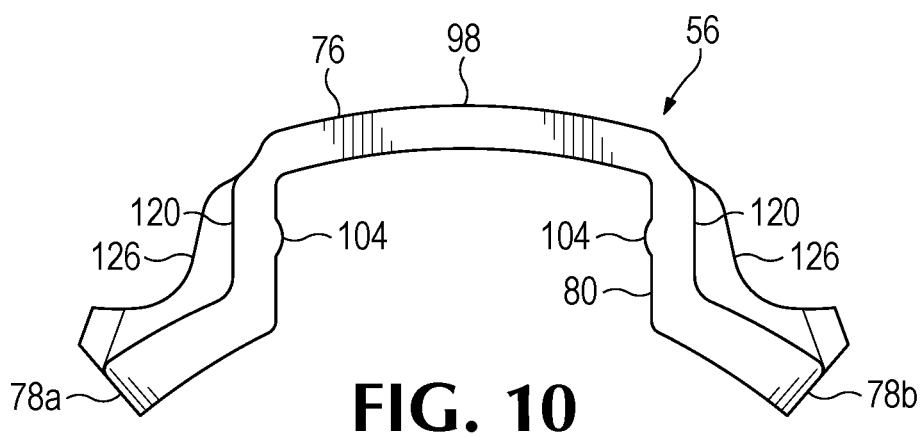
FIG. 10 is an end view of the retainer of FIG. 1 taken parallel to the extension axis on which the plate extends through the retainer.

FIGS. 1 and 2 show fixation system 50 attached to a distal portion of a femur 58 having at least one discontinuity, such as at least one fracture 60, with plate 52 spanning the discontinuity. The system may be utilized to stabilize any suitable portion of any suitable bone. For example, the system may be attached to a bone having at least a portion of an implant 62 extending along a medullary canal thereof, and the implant, plate 52, encircling assembly 54, and/or retainer 56 may be located at mutually overlapping positions along the bone, such as overlapping positions in a shaft region of the bone (also see Section II).

Plate 52 may have any suitable structure and orientation on bone. The plate may be elongated and oriented longitudinally on the bone, as shown. Plate 52 may have an inner surface 64 (also called a bone-facing surface or bottom surface) opposite an outer surface 66 (also called a top surface). The plate also may have a pair of lateral edges 68 (also called lateral sides) located intermediate surfaces 64, 66 and extending between opposite ends of the plate. The plate may define a plurality of apertures 70 to receive fasteners, such as bone screws that attach the plate to bone. Each fastener may be a linear fastener, which may have one or more external threads to engage the plate or bone (or both). Each aperture 70 may extend through plate 52 from inner surface 64 to outer surface 66. Each of the fasteners placed into an aperture 70 independently may or may not lock to the wall of the aperture, such as via an internal thread 72 of the aperture. Each aperture independently may be circular or elongated transversely (e.g., orthogonally) to a through-axis of the aperture, among others. Other exemplary fasteners for engagement of plate 52 include pins, pegs, rivets, staples, wires, retainer 56, or the like. Any suitable number of apertures 70, such as only a subset of the apertures, may receive fasteners that connect plate 52 to bone.

Fixation system 50 may include one or more retainers 56, each of which may be installed over plate 52 at the discretion of the surgeon. Each retainer 56 may be positioned at a selected position along a centerline 74 of plate 52 to couple the plate to bone at that position. (The centerline may be linear or curved.) The position may be selected from a continuous range of permitted axial positions at which the retainer can be installed. The retainer may be introduced where local attachment of the plate to the bone via fasteners placed into apertures 70 is not feasible, not effective, needs reinforcement, or the like. The retainer may be described as a supplemental plate or an attachment plate.

Each retainer 56 may have a body 76 and a pair of mounting regions 78a, 78b interconnected by the body (see FIGS. 3 and 4). The mounting regions may be located opposite one another on opposite sides of body 76. The body may be contoured to be complementary to a section of the plate by defining a recess 80 (interchangeably called a receiving space) in the underside of the body. The recess allows the retainer to be mated with plate 52, such that body 76 receives a section of the plate and straddles the plate. Once the retainer is mated with the plate, body 76 may be located on/adjacent, and optionally in contact with, outer surface 66 and lateral edges 68 to cover a portion of each.

The cross-sectional shape of plate 52 may be sufficiently uniform along at least a portion of its length to allow the retainer to be mated with the plate at each of a plurality of alternative longitudinal positions along the plate, and/or to allow the retainer, once mated, to slide longitudinally along the plate to a desired position. (An alternative longitudinal position of the retainer is shown in phantom outline in FIG. 1.) Mounting regions 78a, 78b of the mated retainer may be disposed respectively on opposite lateral sides of plate 52, and may project away from respective lateral edges 68 of plate 52, and/or in opposite circumferential directions on the bone.

Retainer 56 may be secured to bone via mounting regions 78a, 78b to couple plate 52 to bone (see FIGS. 1-4). Each mounting region may be attached to bone via (a) at least one threaded fastener 82 (which be linear and/or threaded externally), (b) a spanning member 84 extending from one mounting region to the other mounting region such that the spanning member and the retainer cooperatively form encircling assembly 54 that encircles plate 52 and the bone, or (c) both.

Each mounting region 78a, 78b may define one or more apertures to receive fastener(s) 82 and/or spanning member 84. The mounting region may define at least one aperture 86 to operatively receive threaded fastener(s) 82 (see FIG. 4). Each aperture 86 may have an internal thread for threaded engagement with fastener 82. For example, fastener 82 may have an externally-threaded trailing portion 88 that locks the fastener to aperture 86. Alternatively, the fastener may not lock to the aperture because the aperture lacks an internal thread and/or the fastener lacks a complementary external thread. In some embodiments, the system may include a first set of fasteners that lock to apertures 86 via the internal thread thereof, and a second set of fasteners that do not lock to the apertures. The second set of fasteners allow the surgeon to choose the trajectories followed by the fasteners into the bone. In any event, fastener 82 may have an externally threaded shaft 90 to engage bone under the mounting region. The diameter of shaft 90 may be less than that of trailing portion 88. The mounting region also or alternatively may define an aperture 92 sized to receive and engage part of spanning member 84.

The spanning member may include a line 94 and a pair of stop members 96a, 96b. The line may be a length of cable/wire or the like that is capable of following a circumferential path around the bone between mounting regions 78a, 78b. The line may be sufficiently flexible to conform generally to a convex contour of the bone. Each stop member may be any structure having a fixed or fixable position along the line, and sized to prevent passage, completely through aperture 92, of the stop member (and the attached line). One of the stop members may be pre-attached to the line during manufacture (e.g., by crimping, welding, press-fitting, or the like), or both stop members may be attached to the line intra-operatively, among others. The stop members may or may not have the same structure (e.g., may or may not be substantially identical to one another). In some embodiments, at least one of the stop members may be a sleeve through which the line can extend. The sleeve may be deformable (i.e., crimpable) to lock (firmly attach) the sleeve to the line, such that the sleeve can no longer slide along the line.

FIGS. 5-7 show retainer 56 mated with plate 52. A section of plate 52 is located in recess 80 of retainer 56. The retainer has a top portion 98 positioned over outer surface 66 of the plate, and has lateral portions 100 positioned adjacent lateral edges 68 of the plate. The retainer and plate may define complementary mating structures that slidably connect the retainer and plate to one another via a snap-fit connection upon mating (and before the retainer is attached to bone with fasteners 82 and/or spanning member 84). More specifically, the mating structures may include a pair of longitudinal tracks 102 provided by plate 52 that resist removal of retainer 56, when the retainer is urged away from the plate normal to the outer surface of the plate, while guiding movement of the retainer along the plate, parallel to centerline 74 (see FIGS. 2, 3, and 6). In the depicted embodiment, tracks 102 are furrows defined by lateral edges 68 of plate 52, and retainer 56 defines complementary protrusions 104, such as ridges, on lateral portions 100 in recess 80. In other embodiments, the tracks may be formed by protrusions, such as ridges, on plate 52, and complementary indentations may be defined in corresponding lateral wall portions of recess 80. The retainer (and/or the plate) may deform as the retainer is being mated with the plate, to allow the complementary mating structures to be placed into operative interaction. Accordingly, the retainer when first mated with the plate, may provide haptic and/or audible feedback to the surgeon when mating has been completed. The retainer also may need to be deformed to separate the complementary mating structures from one another, thereby permitting removal of the retainer from the plate. In some cases, a tool may be utilized to apply sufficient force for removal.

FIGS. 5-7 illustrate how the retainer can be coupled to femur 58 (or another bone) using spanning member 84 (FIG. 6) and/or fasteners 82 (FIG. 7), while avoiding implant 62 in medullary canal 106 of the femur. FIGS. 6 and 7 compare through-axes 108 defined by apertures 92 used for spanning member 84, with through-axes 110 defined by apertures 86 for threaded fasteners 82. Axes 108 may be tangential with respect to the bone, to guide line 94 of spanning member 84 in a circumferential direction on the bone. This arrangement helps to prevent the line from getting kinked. The term "tangential" for an axis in relation to a bone means substantially following a tangent defined by the bone, such that the axis passes close to the surface of the bone, either missing the bone completely or only passing through the bone peripherally. In contrast, axes 110 may be oriented relatively more radially with respect to the bone, and may pass through opposite sides of the bone, to guide fastener 82 into the bone, optionally while missing medullary canal 106 (and thus implant 62).

The respective orientations of axes 108, 110 also may be contrasted by their relationships to a radial plane 112 and a tangential plane 114 (see FIGS. 6 and 7). Radial plane 112 is centered between mounting regions 78a, 78b and oriented at least generally radially with respect to the bone. The radial plane is parallel to (and optionally contains) an extension axis 116 on which plate 52 extends through retainer 56, and may bisect the retainer. Tangential plane 114 is orthogonal to radial plane 112 and tangential to the bone. Through-axes 108 and 110 may intersect radial plane 112 on opposite sides of tangential plane 114 from one another. More specifically, through-axes 108 may intersect radial plane 112 above the retainer, and through-axes 110 may intersect radial plane 112 below the retainer. The terms "above" and "below" as used herein are defined with the outer/top surface of the plate and retainer facing upward. More specifically, "above" a given element means at a higher elevation than the element, and "below" means at a lower elevation than the element.

The orientation of axes 108, 110 alternatively may be contrasted in an orthogonal projection of the retainer onto a transverse plane 118 that is orthogonal to extension axis 116 (see FIGS. 5-7). In the projection, axes 108 converge above retainer 56 (as in FIG. 6), while a pair of axes 110 from respective mounting regions 78a, 78b converge below retainer 56 (as in FIG. 7).

A pair of axes 108 or 110 may or may not lie in the same plane. Axes 108 may be coplanar with one another, optionally lying in a plane that is parallel to transverse plane 118. Each at least generally converging pair of axes 110 also may be coplanar with one another, again optionally lying in a plane that is parallel to transverse plane 118. In contrast, a pair of axes 108 and 110 defined by respective apertures 86, 92 of the same mounting region 78a or 78b, when projected orthogonally onto transverse plane 118, may be oblique to one another in the projection. The pair of axes may form an angle between one another in the projection of at least about 10, 15, 20, or 25 degrees, among others.

FIGS. 8-12 show various views of retainer 56, which may have reflectional symmetry. As discussed above, the retainer may have a body 76, defining recess 80, and mounting regions 78a, 78b projecting from opposite sides of the body. The body may be generally U-shaped in end view and cross-section (see FIG. 10), with a top portion 98 interconnecting a pair of depending legs 120. Each mounting region may include a foot formed on the end of each leg and configured to be disposed on bone. Each leg and attached mounting region (or foot) form a lateral portion 100 of the retainer (also see FIG. 6). Each foot may be divided by openings, such as slits 122, into a plurality of mounting sections or tabs 124a, 124b, 124c, each defining a respective aperture (i.e., aperture 86 or 92) (see FIG. 9). In the depicted embodiment, mounting tab 124b to receive line 94 is located between a pair of mounting tabs 124a, 124c to receive respective fasteners 82. The presence of more than one mounting tab in the mounting region can be advantageous because this configuration allows the tabs to be deformed independently of one another (e.g., to adjust the orientation of at least one tab), and to have a different resistance to deformation from one another. For example, in the depicted embodiment, each mounting tab 124*b* is strengthened and stabilized by a pair of ribs 126 that protrude from the outer side of each leg and extend continuously to the mounting tab (see FIGS. 8 and 9). Ribs 126 also or alternatively may form opposite sides of a channel 128 that joins aperture 92. The channel may guide placement of a stop member 96*a* or 96*b* into aperture 92 during installation of the retainer and/or limit excessive movement of the stop member.

Figure 11:
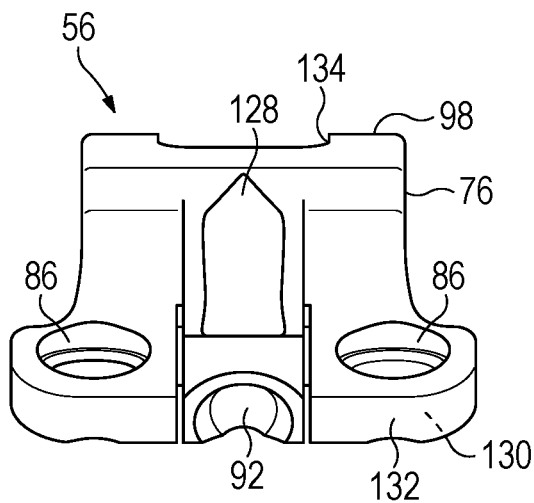
FIG. 11 is a side view of the retainer of FIG. 1 taken orthogonal to FIG. 10.
Figure 12:
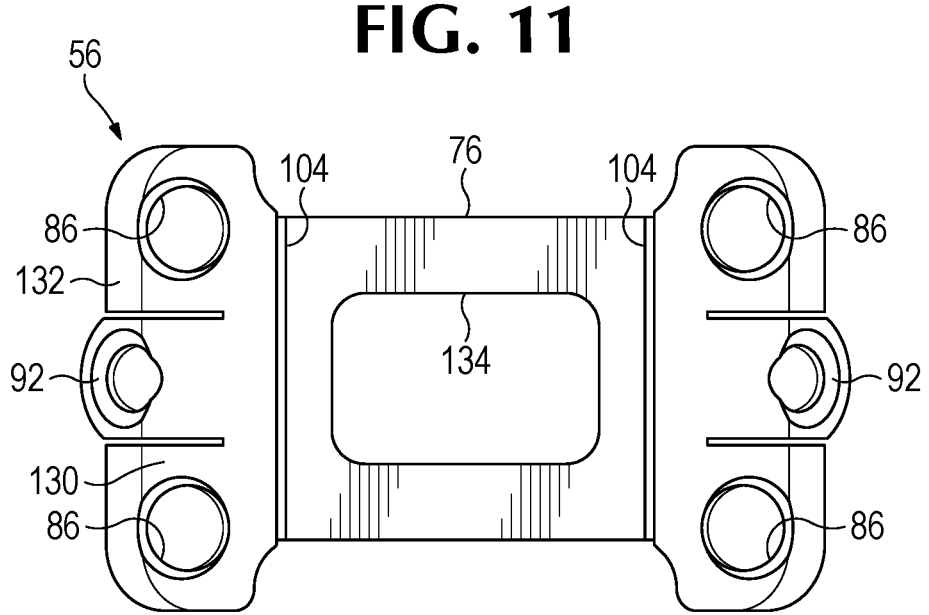
FIG. 12 is a bottom view of the retainer of FIG. 1.
Figure 13:
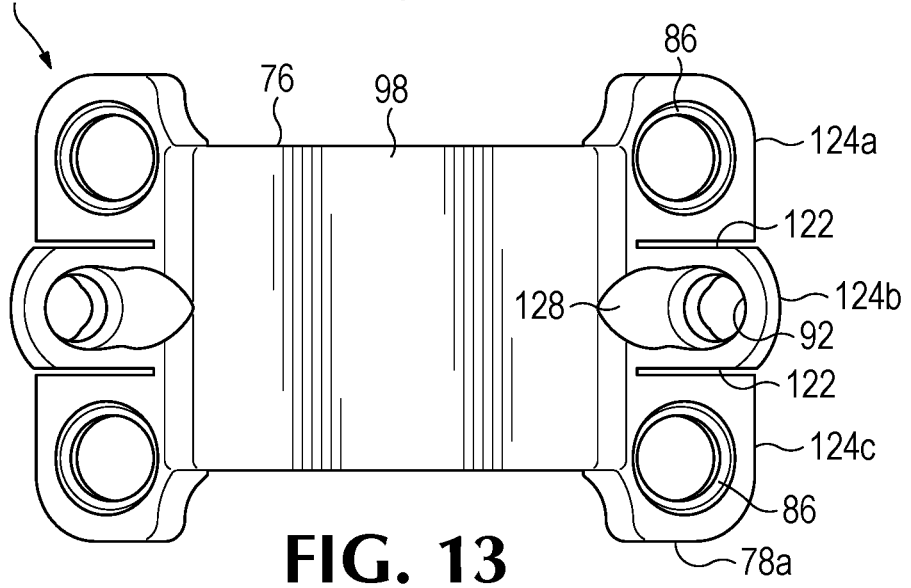
FIG. 13 is a top view of another exemplary retainer for the fixation system of FIG. 1.

FIGS. 11 and 12 further illustrate the different orientations of apertures 86 and 92. Each mounting region or foot has at least one inner surface region 130 to face bone, and at least one lateral surface regions 132 forming a lateral edge of the retainer. The bottom end of each aperture 86 may be formed at least predominantly in an inner surface region 130, while the bottom end of each aperture 92 may be formed at least predominantly in a lateral surface region 132.

Retainer 56 may have a window 134 defined as a large opening by top portion 98. The presence of the window increases the flexibility of the retainer, to facilitate deformation of the retainer that may be needed when the retainer is mated with the plate (see above). Alternatively, the window may be omitted to increase the strength of the retainer (see FIG. 13).

Figure 14:
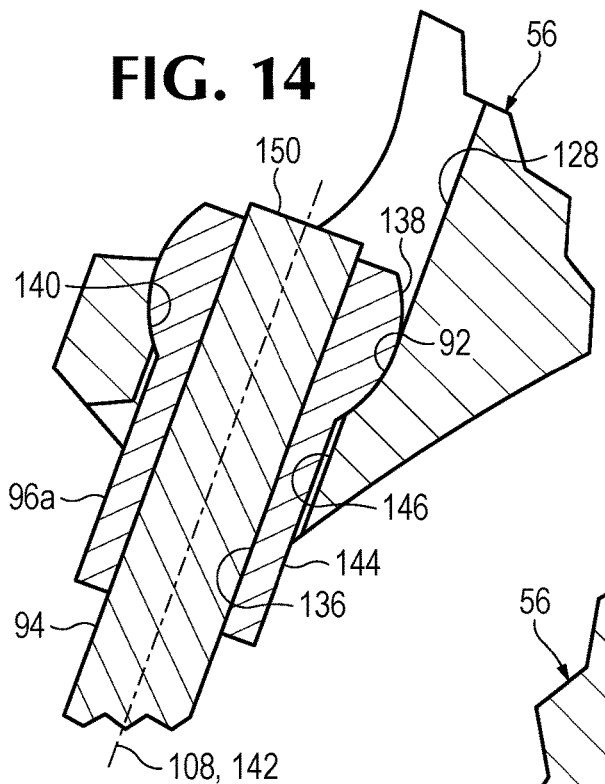
FIG. 14 is a magnified, fragmentary view corresponding to FIG. 6, taken around one of the stop members of the encircling assembly.
Figure 15:
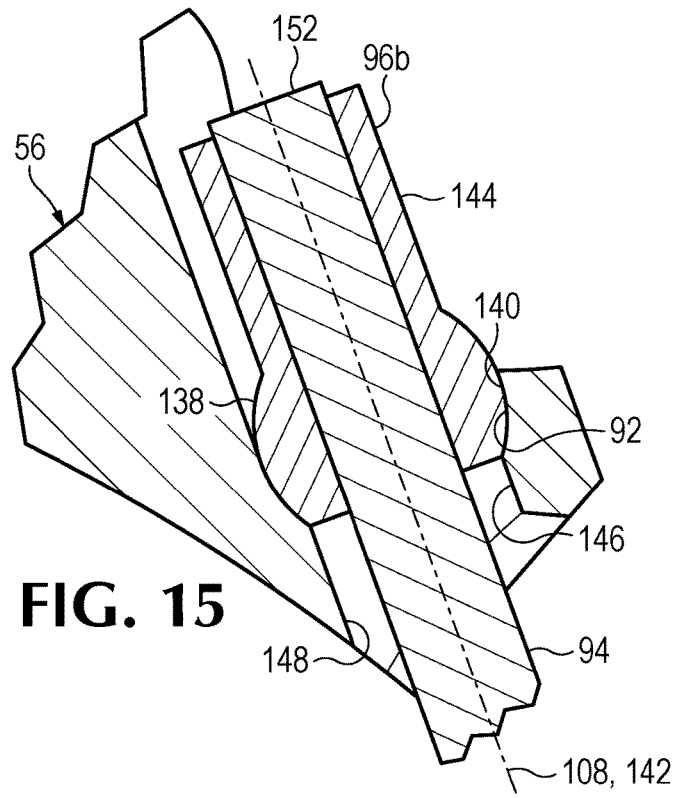
FIG. 15 is another magnified, fragmentary view corresponding to FIG. 6, taken around the other stop member of the encircling assembly.
Figure 16:
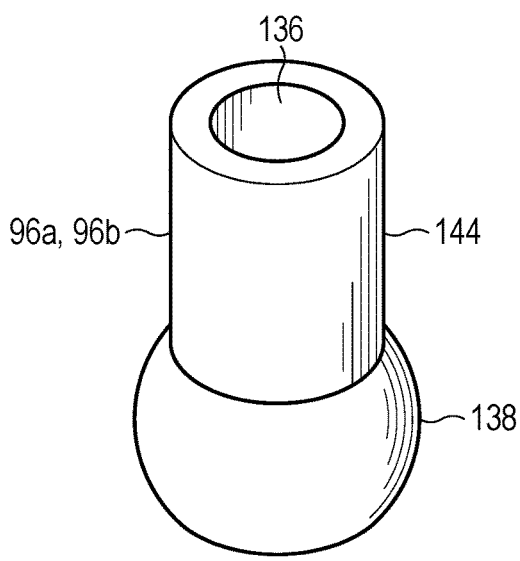
FIG. 16 is an isometric view of a stop member of the fixation system of FIG. 1 taken in isolation.

FIGS. 14-16 show further aspects of stop members 96*a*, 96*b* and exemplary relationships between the stop members, retainer 56, and line 94. Each stop member may be sized to prevent complete passage of the stop member through aperture 92. One or both stop members may be a sleeve defining a through-bore 136 sized in correspondence with the diameter of line 94, to allow the line to slide through the sleeve. The stop member may have an enlarged bearing portion 138, which may be spherical, to contact a complementary wall region 140 of aperture 92. The sleeve and retainer may be configured to permit bearing portion 138 to slide on wall region 140 of aperture 92 through a range of orientations of a long axis 142 defined by the stop member. The stop member also may have a crimp portion 144 at which the stop member is configured to be crimped. The crimp portion may have a smaller maximum diameter than bearing portion 138. The crimp portion may be non-spherical, and may be elongated and/or cylindrical. In some embodiments, as described further below, each stop member may be installed in either of two opposite orientations on line 94 and/or the stop members may be inverted with respect to one another when installed.

FIGS. 14 and 15 show an exemplary structure for aperture 92. The aperture may have concave spherical wall region 140 disposed outward (along through-axis 108) of a cylindrical region 146, which, like aperture 86, may have an internal thread 148. (The presence of an internal thread may permit aperture 92 to be used alternatively with fasteners 82 and spanning member 84. Channel 128 may extend continuously from wall region 140 and may be cylindrical, with the same radius of curvature as wall region 140.

FIGS. 14 and 15 also illustrate exemplary configurations for stop members 96*a* and 96*b* in respective mounting regions 78*a* and 78*b* of retainer 56. The stop members may be inverted relative to one another, as shown, to position crimp portion 144 below (FIG. 14) or above (FIG. 15) bearing portion 138. In other embodiments, the stop members may not be identical to one another.

Stop member 96*a* (or a different stop member) may be pre-attached to line 94, such as by deforming crimp portion 144, optionally before either end region of the line is passed through aperture 92. The stop member may be oriented such that crimp portion 144 is farther than bearing portion 138 from a first end region 150 of the line, and closer than bearing portion 138 to a longitudinally central section of the line. Accordingly, in the installed configuration of FIG. 14, bearing portion 138 is in contact with spherical wall region 140 of aperture 92 above crimp portion 144. The crimp portion may be disposed adjacent cylindrical region 146 of aperture 92 and may project out of the lower end of the aperture. The orientation of stop member 96*a* minimizes tissue irritation.

Stop member 96*b* may be attached to line 94 after stop member 96*a* is located in corresponding aperture 92. A second, opposite end region 152 of line 94 may be fed around the bone, and through aperture 92 and stop member 96*b*. The line may be tensioned, and crimp portion 144 deformed to lock the stop member to the line. Line 94 then may be cut to remove at least part of second end region 152, if any, that protrudes from crimp portion 144 of stop member 96*b*.

Each stop member may or may not be permitted to pivot about a center of curvature of bearing portion 138. This pivotal motion permits line 94 to more closely follow the contour of the bone near the retainer and allows the stop member to be operatively engaged with the wall of aperture 92 in a range of orientations. In FIG. 14, the outer diameter of crimp portion 144 may be only slightly less than the inner diameter of aperture 92 at cylindrical region 146, to restrict pivotal motion of the bearing portion, or may be significantly less to permit pivotal motion. In FIG. 15, the diameter of line 94 is significantly less than the corresponding inner diameter of aperture 92 at cylindrical region 146, allowing pivotal motion of stop member 96*b* to change the orientation at which line 94 extends from retainer 56.

II. Methods of Bone Fixation and Plate Attachment

This section describes exemplary methods of bone fixation and plate attachment implemented with the systems of the present disclosure. The method steps of this section may be performed in any suitable order and combination, and may be modified by, or combined with, any other suitable aspects of the present disclosure.

A bone to be fixed may be selected. The method may be performed on any suitable bone, and on any suitable portion thereof, such as a proximal portion, a central portion, a distal portion, or a combination thereof, among others. Exemplary bones that may be selected include a long bone of a limb, such as a femur, tibia, fibula, humerus, radius, or ulna. The bone may have any suitable discontinuity or structural weakness, such as at least one fracture, cut, nonunion, or the like. The bone may contain at least a portion of an implant in a medullary canal of the bone. The implant may be a prosthesis this is attached to the bone, replaces a missing portion of the bone, and/or provides an articulation surface of a joint. The implant alternatively may be an intramedullary nail.

An incision may be created through overlying soft tissue to access the selected bone. The bone may be manipulated to reposition bone fragments (e.g., to approximate the relative anatomical location of the fragments), such as to set a fracture. Manipulation of bone fragments may be performed before and/or after the incision is created.

A plate may be selected for stabilizing the bone. The plate may be elongated and/or may have any combination of the plate features described elsewhere herein. The plate may be described as a main plate. The plate may be placed through the incision and onto the bone, such that the plate spans a discontinuity in the bone.

The plate may be attached to the bone with one or more fasteners, such as at least one screw, peg, pin, wire, cable, rivet, and/or the like. Each fastener independently may extend into bone directly under the plate from an aperture (a through-hole) thereof (e.g., in the case of a screw, peg, or pin), or may extend over the plate and around the bone (e.g., in the case of a wire or cable). The fastener may engage the plate, and may or may not lock to the plate, such as via threaded engagement. In some embodiments, the plate may be attached provisionally to the bone with at least one tool, such as at least one clamp, before the plate is attached with the one or more fasteners and/or one or more encircling assemblies including a retainer (see below).

At least one retainer may be selected for attaching the plate to the bone, and a suitable longitudinal position for each retainer along the plate may be selected. The number and position(s) of retainers to be used in the method may be selected at any suitable time, such as before and/or after attaching the plate to the bone with one or more fasteners (and/or one or more tools) that engage the plate. In some embodiments, positions for retainers may be based on one or more locations at which the one or more fasteners are engaged with the plate, and may be offset along the plate from these locations, namely, at longitudinal positions of the plate at which no fasteners attach the plate to bone. Each retainer may be a supplemental plate.

The selected retainer may be placed onto the plate, optionally after the plate has been disposed on the bone and attached to the bone with one or more fasteners and/or tools. The retainer may be mated with the plate at a pre-selected target position along the plate, or the retainer may be mated at a longitudinally offset position of the plate and then moved longitudinally along the plate to the target position, among others.

One or more fasteners for the retainer may be selected. The fasteners may be selected from a set of fasteners including at least linear fastener and at least one spanning member.

Each fastener selected for the retainer may be operatively disposed to couple the retainer to the bone. At least one linear fastener (e.g., a screw, pin, peg, rivet, etc.) may be placed into the bone from an aperture of the retainer. The linear fastener may engage the retainer, and may or may not lock to the aperture, such as via threaded engagement. In exemplary embodiments, the linear fastener avoids (i.e., does not extend through) the plate. In some embodiments, the retainer may have a pair of mounting regions (see Section I), and at least one threaded fastener may be operatively disposed in an aperture of each mounting region. In some embodiments, at least two threaded fasteners may be operatively disposed in at least one or both of the mounting regions. A spanning member also or alternatively may be connected operatively to the retainer, such that the retainer and spanning member collectively encircle the bone.

The spanning member may be installed by any suitable procedure. In some embodiments, a spanning member selected for installation may include (i) a line having a first stop member pre-mounted to a first end region of the line and (ii) a second stop member that is separate from, and not yet assembled with, the line. The line may be fed through a first aperture of a first mounting region of the retainer, starting at a second end region of the line opposite the first end region, until the first stop member contacts the retainer at the first aperture to restrict advancement of the line through the first aperture. The second end region may be fed around the bone and through a second aperture of a second mounting region of the retainer. The second stop member may be placed onto the second end region of the line and into the second aperture, the line tensioned, and the second stop member crimped to lock the second stop member to the line. When the stop member is crimped, both stop members may be seated in their respective apertures and collectively may prevent release of tension on the line. The line may be cut to remove a length of the line that is protruding from the top of the second stop member.

III. Composition of System Components

The plates, retainers, fasteners, lines, and stop members of the present disclosure may have any suitable composition. Each may be formed independently and at least partially or completely of any suitable biocompatible material(s) and/or bioresorbable (bioabsorbable) material(s). Illustrative biocompatible materials that may be suitable include (1) metal (for example, titanium or titanium alloy, cobalt-chrome alloy, stainless steel, etc.); (2) polymer/plastic (for example, ultra-high molecular weight polyethylene (UHMWPE), polymethylmethacrylate (PMMA), polytetrafluoroethylene (PTFE), polyetheretherketone (PEEK), and/or PMMA/polyhydroxyethylmethacrylate (PHEMA)); (3) bioresorbable material or polymer/plastic (for example, polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, poly(hydroxyalkanoate)s of the PHB-PHV class, other bioresorbable polyesters, and/or natural polymers (such as collagen or other polypeptides, polysaccharides (e.g., starch, cellulose, and/or chitosan), any copolymers thereof, etc.)); (4) bone material or bone-like material (e.g., bone chips, calcium phosphate crystals (e.g., hydroxyapatite, carbonated apatite, etc.)); or (5) any combination thereof. In exemplary embodiments, the plate, each retainer, each fastener, each line, and each stop member is formed of metal, of the same or different composition.

IV. Examples

The following examples describe selected embodiments of the systems and methods of the present disclosure as series of numbered paragraphs.

Example 1. Selected Embodiments A

Paragraph 1. A method of attaching a plate to bone, the method comprising, in any order: (A) disposing a plate on a bone; (B) placing a retainer over the plate, such that the retainer straddles the plate, and such that a first mounting region and a second mounting region of the retainer project away from opposite lateral edges of the plate; and (C) connecting the retainer to the bone using a spanning member extending from an aperture of the first mounting region to an aperture of the second mounting region, such that the retainer and the spanning member collectively encircle the bone.

Paragraph 2. The method of paragraph 1, further comprising a step of placing a linear fastener into the bone from another aperture of each mounting region.

Paragraph 3. The method of paragraph 2, wherein the step of placing a linear fastener includes a step of engaging the mounting region with the linear fastener.

Paragraph 4. The method of paragraph 3, wherein the step of engaging the mounting region includes a step of locking the linear fastener to the mounting region.

Paragraph 5. The method of any of paragraphs 1 to 4, wherein the spanning member includes a line and a stop member, and wherein the step of connecting the retainer includes a step of placing an end region of the line through the aperture of the second mounting region, a step of disposing the stop member on the line, and a step of crimping the stop member to firmly attach the stop member to the line.

Paragraph 6. The method of paragraph 5, wherein the stop member includes a spherical portion, and wherein the spherical portion is seated in the aperture of the second mounting region after the step of connecting.

Paragraph 7. The method of paragraph 6, wherein the spherical portion of the stop member is seated against a spherical wall region of the aperture of the second mounting region after the step of connecting.

Paragraph 8. The method of any of paragraphs 5 to 7, wherein the stop member includes a sleeve having a bearing portion configured to be seated in the aperture of the second mounting region over a range of orientations of a through-axis defined by the stop member, and wherein the sleeve also has a distinct crimp portion configured to be crimped to lock the stop member to the line.

Paragraph 9. The method of paragraph 8, wherein the bearing portion is configured to be seated in the aperture over a range of orientations of the through-axis in each of a pair of orthogonal planes.

Paragraph 10. The method of paragraph 8 or 9, wherein the bearing portion is spherical, and wherein the crimp portion is non-spherical.

Paragraph 11. The method of any of paragraphs 8 to 10, wherein the crimp portion is elongated.

Paragraph 12. The method of any of paragraphs 8 to 11, wherein the crimp portion is cylindrical.

Paragraph 13. The method of any of paragraphs 1 to 12, wherein the spanning member includes a length of cable or wire.

Paragraph 14. The method of any of paragraphs 1 to 13, wherein the step of connecting the retainer includes a step of selecting a line having a stop member pre-attached to a first end region of the line, a step of placing an opposite, second end region of the line through an aperture of the first mounting region and then through an aperture of the second mounting region, the aperture of the first mounting region being sized to prevent passage of the stop member completely through the aperture, and a step of firmly attaching another stop member to a second end region of the line after the step of placing an opposite, second end region of the line.

Paragraph 15. The method of any of paragraphs 1 to 14, wherein each of the first mounting region and the second mounting region of the retainer defines an aperture from which the spanning member extends after the step of connecting and also defines another aperture having an internal thread.

Paragraph 16. The method of any of paragraphs 1 to 15, further comprising a step of tensioning a line of the spanning member, wherein the line has a tensioned configuration when the step of connecting is complete.

Paragraph 17. The method of any of paragraphs 1 to 16, wherein the step of disposing a plate on a bone includes a step of disposing a plate on a femur.

Paragraph 18. The method of any of paragraphs 1 to 17, wherein the step of placing a retainer positions the retainer over an implant extending along a medullary canal of the bone.

Paragraph 19. A system for attaching a plate to bone, comprising: (A) a plate configured to be disposed on a bone; (B) a retainer having a first mounting region opposite a second mounting region, the retainer being configured to straddle the plate such that the first mounting region and the second mounting region project away from opposite lateral edges of the plate, each of the first mounting region and the second mounting region defining an aperture; (C) a line configured to extend from the aperture of the first mounting region to the aperture of the second mounting region, such that the retainer and the line collectively encircle a bone; and (D) a sleeve configured to be received on the line and crimped to lock the sleeve to the line.

Paragraph 20. The system of paragraph 19, wherein each of the first mounting region and the second mounting region defines another aperture, and wherein the another aperture has an internal thread.

Paragraph 21. The system of paragraph 20, wherein the aperture and the another aperture of each mounting region define respective through-axes that are non-parallel to one another.

Paragraph 22. The system of any of paragraphs 19 to 21, further comprising a stop member pre-attached to the line and configured to prevent passage of the stop member completely through the aperture of at least one of the first mounting region and the second mounting region.

Paragraph 23. The system of paragraph 22, wherein the stop member is crimped onto the line.

Paragraph 24. The system of any of paragraphs 19 to 23, wherein the sleeve includes a spherical portion.

Paragraph 25. The system of paragraph 24, wherein the aperture of at least one of the first and second mounting regions has a spherical wall region against which the spherical portion is configured to be seated.

Paragraph 26. The system of any of paragraphs 19 to 25, wherein the sleeve has a bearing portion configured to be seated in an aperture of one of the mounting regions, and wherein the sleeve also has a distinct crimp portion that is configured to be crimped to lock the sleeve to the line.

Paragraph 27. The system of any of paragraphs 19 to 26, wherein the crimp portion is cylindrical, elongated, or both cylindrical and elongated.

Paragraph 28. The system of any of paragraphs 19 to 27, wherein the retainer is configured to be operatively disposed on the plate at each of a plurality of alternative longitudinal positions along the plate.

Example 2. Selected Embodiments B

Paragraph 1. A system for fixing bone, comprising: (A) an elongated plate configured to be disposed longitudinally on a bone; (B) a retainer having a body interconnecting a pair of mounting regions, the body defining a recess, each mounting region defining a first aperture and a second aperture, the retainer being configured to be mated with the plate to position a section of the plate in the recess such that the retainer straddles the plate; (C) a line configured to extend between the first apertures, such that the retainer and the line collectively encircle the plate and the bone, the line including wire and/or cable; and (D) a stop member configured to be received on an end region of the line that has passed through the first aperture of one of the mounting regions, and to be crimped to firmly attach the stop member to the line, thereby preventing the end region from passing back through the first aperture of the one mounting region.

Paragraph 2. The system of paragraph 1, wherein the second aperture of each mounting region has an internal thread, and wherein the system further comprises a plurality of fasteners each having an external thread that is complementary to the internal thread.

Paragraph 3. The system of paragraph 1 or paragraph 2, where the first aperture of each mounting region is configured to define a through-axis that is tangential to the bone, and wherein the second aperture of each mounting region is configured to define a through-axis that passes through opposite sides of the bone while avoiding a medullary canal thereof.

Paragraph 4. The system of any one of paragraphs 1 to 3, wherein mating the retainer with the plate connects the retainer to the plate, and wherein the plate defines a pair of longitudinal tracks configured to permit the retainer to slide along the plate after the retainer has been connected to the plate by mating.

Paragraph 5. The system of paragraph 4, wherein the retainer is configured to be connected to the plate via a snap-fit connection.

Paragraph 6. The system of paragraph 4 or paragraph 5, wherein the retainer is configured to be deformed as the retainer is being mated with the plate.

Paragraph 7. The system of any one of paragraphs 1 to 6, wherein the stop member includes a crimp portion and a spherical portion, wherein the crimp portion is configured to be crimped to lock the stop member to the line, and wherein the first aperture of the one mounting region has a spherical wall region that is complementary to the spherical portion of the stop member.

Paragraph 8. The system of any one of paragraphs 1 to 7, wherein the stop member is a first stop member, further comprising a second stop member firmly attached to an opposite end region of the line and configured to prevent passage of such end region through the first aperture of the other mounting region.

Paragraph 9. A system for fixing bone, comprising: (A) an elongated plate configured to be disposed longitudinally on a bone; and (B) a retainer having a body interconnecting a pair of mounting regions, the body defining a recess, each mounting region defining a first aperture and a second aperture, the retainer being configured to be mated with the plate to position a section of the plate in the recess such that the retainer straddles the plate; wherein the first aperture of each mounting region is configured to define a through-axis oriented tangential to the bone, and wherein the second aperture of each mounting region is configured to define a through-axis passing through opposite sides of the bone while avoiding a medullary canal thereof.

Paragraph 10. The system of paragraph 9, wherein the plate has a pair of longitudinal tracks at which the retainer is configured to be slidably connected to the plate by mating the retainer with the plate.

Paragraph 11. The system of paragraph 10, wherein the pair of longitudinal tracks includes a pair of longitudinal furrows, and wherein the retainer defines a pair of protrusions configured to be received in the pair of longitudinal furrows when the retainer is mated with the plate.

Paragraph 12. The system of any one of paragraphs 9 to 11, wherein the second aperture of each mounting region has an internal thread, and wherein the system further comprises a plurality of fasteners each having an external thread complementary to the internal thread.

Paragraph 13. The system of paragraph 12, wherein the plurality of fasteners is a first set of threaded fasteners, and wherein the system further comprises a second set of threaded fasteners each configured to be received in the second aperture of either mounting region and having no external thread that is complementary to the internal thread.

Paragraph 14. The system of any one of paragraphs 9 to 13, further comprising a line configured to extend between the first apertures such that the retainer and the line collectively encircle the plate and the bone, wherein the line includes wire and/or cable.

Paragraph 15. The system of paragraph 14, further comprising a stop member configured to be received on an end region of the line and crimped to lock the stop member to the line, wherein the stop member has a maximum diameter that is greater than a minimum diameter of the first aperture of at least one of the mounting regions.

Paragraph 16. The system of paragraph 15, wherein the stop member and the first aperture of the at least one mounting region having complementary spherical surface regions.

Paragraph 17. A method of bone fixation, the method comprising, in any order: (A) disposing a plate longitudinally on a bone; (B) selecting a retainer having a body interconnecting a pair of mounting regions, the body defining a recess, each mounting region having a first aperture and a second aperture, the first aperture defining a through-axis configured to be oriented tangential to the bone, and the second aperture defining a through-axis configured to pass through opposite sides of the bone while avoiding a medullary canal thereof; (C) mating the retainer and the plate with one another to position a section of the plate in the recess, such that the retainer straddles the plate; and (D) securing the plate to the bone, at least in part by coupling the retainer to the bone using a line extending between the first apertures of the mounting regions and/or using threaded fasteners placed into the bone from the second apertures of the mounting regions.

Paragraph 18. The method of paragraph 17, wherein the mounting regions project from the body in opposite circumferential directions on the bone after the step of securing.

Paragraph 19. The method of paragraph 17 or paragraph 18, wherein the step of securing includes a step of coupling the retainer to the bone using a line including wire or cable, such that the retainer and the line collectively encircle the plate and the bone.

Paragraph 20. The method of paragraph 19, wherein the step of coupling the retainer includes a step of passing an end region of the line through the first aperture of one of the mounting regions, a step of disposing a stop member on the end region, and a step of crimping the stop member to firmly attach the stop member to the end region, such that the stop member prevents the end region from passing back through the first aperture of the one mounting region.

Paragraph 21. The method of paragraph 20, wherein the stop member includes a convex spherical portion, and wherein the convex spherical portion is engaged with a complementary wall region of the first aperture of the one mounting region after the step of coupling.

Paragraph 22. The method of any one of paragraphs 19 to 21, wherein the stop member includes a sleeve having a convex spherical portion and a crimp portion, and wherein the step of coupling includes a step of crimping the crimp portion.

Paragraph 23. The method of any one of paragraphs 19 to 22, wherein the retainer is coupled to the bone using a pair of stop members firmly attached to opposite end regions of the line and urged against the pair of mounting regions at the first apertures by tension on the line.

Paragraph 24. The method of any one of paragraphs 19 to 23, wherein a radial plane is centered between the mounting regions, wherein the through-axes defined by the first apertures intersect the plane above the retainer, and wherein the through-axes defined by the second apertures intersect the plane below the retainer.

Paragraph 25. The method of any one of paragraphs 17 to 24, wherein the step of mating connects the retainer to the plate such that the retainer is slidable along a pair of longitudinal tracks defined by the plate.

Paragraph 26. The method of paragraph 25, wherein the pair of longitudinal tracks includes a pair of longitudinal furrows, wherein the body of the retainer defines a pair of protrusions, and wherein the step of mating includes a step of placing the pair of protrusions in the pair of longitudinal grooves.

Paragraph 27. The method of paragraph 25 or paragraph 26, wherein the step of mating includes a step of deforming the retainer.

Paragraph 28. A system for fixing bone, comprising: (A) an elongated plate configured to be disposed longitudinally on a bone; (B) a retainer having a body interconnecting a pair of mounting regions, the body defining a recess, each mounting region defining an aperture, the retainer being configured to be mated with the plate to position a section of the plate in the recess such that the retainer straddles the plate; (C) a line configured to extend between the apertures, such that the retainer and the line collectively encircle the plate and the bone, the line including wire and/or cable; and (D) a stop member configured to be received on an end region of the line that has passed through the aperture of one of the mounting regions, and to be crimped to firmly attach the stop member to the line, thereby preventing the end region from passing back through the aperture of the one mounting region.

Paragraph 29. A system for fixing bone, comprising: (A) an elongated plate configured to be disposed longitudinally on a bone; and (B) a retainer having a body interconnecting a pair of mounting regions, the body defining a recess, each mounting region defining an aperture, the retainer being configured to be mated with the plate to position a section of the plate in the recess such that the retainer straddles the plate; wherein the aperture of each mounting region is configured to define a through-axis oriented tangential to the bone, and wherein the apertures are configured to receive a line that, collectively with the retainer, encircles the plate and bone.

Paragraph 30. A method of bone fixation, the method comprising, in any order: (A) disposing a plate longitudinally on a bone; (B) selecting a retainer having a body interconnecting a pair of mounting regions, the body defining a recess, each mounting region having an aperture defining a through-axis configured to be oriented tangential to the bone; (C) mating the retainer and the plate with one another to position a section of the plate in the recess, such that the retainer straddles the plate; and (D) securing the plate to the bone, at least in part by coupling the retainer to the bone using a line extending between the apertures of the mounting regions such that the retainer and the line collectively encircle the plate and the bone.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A system for fixing bone, comprising:
   an elongated plate configured to be disposed longitudinally on a bone;
   a retainer having a body interconnecting a pair of mounting regions, the body defining a recess, each mounting region defining a first aperture and a second aperture, the retainer being configured to be mated with the plate to position a section of the plate in the recess such that the retainer straddles the plate;
   a line configured to extend between the first apertures, such that the retainer and the line collectively encircle the plate and the bone, the line including wire and/or cable; and
   a stop member configured to be received on an end region of the line that has passed through the first aperture of one of the mounting regions, and to be crimped to firmly attach the stop member to the line, thereby preventing the end region from passing back through the first aperture of the one mounting region;
   wherein the stop member includes a crimp portion and a spherical portion, wherein the crimp portion is configured to be crimped to lock the stop member to the line, and wherein the first aperture of the one mounting region has a spherical wall region that is complementary to the spherical portion of the stop member.

2. The system of claim 1, wherein the second aperture of each mounting region has an internal thread, and wherein the system further comprises a plurality of fasteners each having an external thread that is complementary to the internal thread.

3. The system of claim 1, where the first aperture of each mounting region is configured to define a through-axis that is tangential to the bone, and wherein the second aperture of each mounting region is configured to define a through-axis that passes through opposite sides of the bone while avoiding a medullary canal thereof.

4. The system of claim 1, wherein mating the retainer with the plate connects the retainer to the plate, and wherein the plate defines a pair of longitudinal tracks configured to permit the retainer to slide along the plate after the retainer has been connected to the plate by mating.

5. The system of claim 4, wherein the retainer is configured to be connected to the plate via a snap-fit connection.

6. The system of claim 4, wherein the retainer is configured to be deformed as the retainer is being mated with the plate.

7. The system of claim 1, wherein the stop member is a first stop member, the system further comprising a second stop member firmly attached to an opposite end region of the line and configured to prevent passage of such end region through the first aperture of the other mounting region.

8. A system for fixing bone, comprising:
- an elongated plate configured to be disposed longitudinally on a bone; and
- a retainer having a body interconnecting a pair of mounting regions, the body defining a recess, each mounting region defining a first aperture and a second aperture, the retainer being configured to be mated with the plate to position a section of the plate in the recess such that the retainer straddles the plate;
- a line configured to extend between the first apertures such that the retainer and the line collectively encircle the plate and the bone, wherein the line includes wire and/or cable; and
- a stop member configured to be received on an end region of the line and crimped to lock the stop member to the line;
- wherein the stop member has a maximum diameter that is greater than a minimum diameter of the first aperture of at least one of the mounting regions, wherein the stop member and the first aperture of the at least one mounting region having complementary spherical surface regions,
- wherein the first aperture of each mounting region is configured to define a through-axis oriented tangential to the bone, and wherein the second aperture of each mounting region is configured to define a through-axis passing through opposite sides of the bone while avoiding a medullary canal thereof.

9. The system of claim 8, wherein the plate has a pair of longitudinal tracks at which the retainer is configured to be slidably connected to the plate by mating the retainer with the plate.

10. The system of claim 8, wherein the second aperture of each mounting region has an internal thread, and wherein the system further comprises a plurality of fasteners each having an external thread complementary to the internal thread.

* * * * *